United States Patent
Chang et al.

(10) Patent No.: US 12,000,825 B2
(45) Date of Patent: Jun. 4, 2024

(54) METHOD OF SELECTING STEM CELLS HAVING ABILITY TO PRODUCE EXTRACELLULAR VESICLES WITH HIGH EFFICIENCY USING ACTIVATION OF PROTEASE-ACTIVATED RECEPTOR-MEDIATED SIGNALING PATHWAYS

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); Dong Kyung Sung, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 956 days.

(21) Appl. No.: 16/961,851

(22) PCT Filed: Apr. 28, 2020

(86) PCT No.: PCT/KR2020/005599
§ 371 (c)(1),
(2) Date: Jul. 13, 2020

(87) PCT Pub. No.: WO2020/222503
PCT Pub. Date: Nov. 5, 2020

(65) Prior Publication Data
US 2021/0255169 A1    Aug. 19, 2021

(30) Foreign Application Priority Data
Apr. 29, 2019  (KR) .................. 10-2019-0049898
Apr. 27, 2020  (KR) .................. 10-2020-0050893

(51) Int. Cl.
*G01N 33/50*     (2006.01)
*C12N 5/0775*    (2010.01)
*G01N 33/573*    (2006.01)

(52) U.S. Cl.
CPC ....... *G01N 33/5023* (2013.01); *C12N 5/0665* (2013.01); *G01N 33/573* (2013.01); *C12N 2501/734* (2013.01); *G01N 2333/974* (2013.01)

(58) Field of Classification Search
None
See application file for complete search history.

(56) References Cited

U.S. PATENT DOCUMENTS

2017/0119682 A1    5/2017    De La Rosa et al.

FOREIGN PATENT DOCUMENTS

| JP | 2017-500033 A    | 1/2017  |
|----|------------------|---------|
| KR | 10-1643825 B1    | 7/2016  |
| KR | 10-2017-0122650 A| 11/2017 |

OTHER PUBLICATIONS

McCoy et al. "PAR1 and PAR2 Couple to Overlapping and Distinct Sets of G Proteins and Linked Signaling Pathways to Differentially Regulate Cell Physiology" (2010), Mol Pharmacology, vol. 77: 1005-1015. (Year: 2010).*
Tang et al. "Comparison of isolation methods of exosomes and exosomal RNA from cell cuture medium and serum" 2017, Internatl J Molecular Med: vol. 40: 834-844. (Year: 2017).*
Shaun R. Coughlin, "Thrombin signaling and protease-activated receptors", Nature, vol. 407, p. 258-264, Sep. 14, 2000.
Jin Chen et al., "Thrombin promotes fibronectin secretion by bone marrow mesenchymal stem cells via the protease-activated receptor mediated signaling pathways", Stem Cell Research & Therapy, vol. 5, No. 36, p. 1-11, Mar. 17, 2014.
Carolina Villarroya-Beltri et al., "Sorting it out: Regulation of exosome loading", Seminars in Cancer Biology., vol. 28, Oct. 1, 2014 (Oct. 1, 2014), pp. 3-13, XP055698382, US.
Extended European Search Report From Corresponding European Application No. 20799495.5, Dated May 26, 2023.
Office Action From Corresponding Japanese Application No. 2021-563128, Dated Apr. 24, 2023.
Office Action from corresponding Japanese Application No. 2021-563128 , dated Nov. 14, 2022.
International Search Report dated Aug. 7, 2020, issued in International Patent Application No. PCT/KR2020/005599.
Written Opinion dated Aug. 7, 2020, issued in International Patent Application No. PCT/KR2020/005599.

(Continued)

*Primary Examiner* — Teresa E Knight
(74) *Attorney, Agent, or Firm* — Harness, Dickey & Pierce, P.L.C.

(57) ABSTRACT

The present disclosure relates to a method of selecting stem cells having the ability to produce extracellular vesicles with high efficiency, the method including the step of measuring the activity of protease-activated receptor (PAR)-mediated signaling pathways, stem cells selected by the method, and a method of screening an inducer for the production of extracellular vesicles. According to the present disclosure, upon treatment of stem cells with thrombin, the production of extracellular vesicles in the stem cells and the levels of proteins in the extracellular vesicles are significantly increased via PAR-mediated signaling pathways, and thus stem cells having the ability to produce extracellular vesicles with high efficiency can be efficiently selected by treating stem cells with thrombin and measuring an activation level of a PAR-mediated signaling pathway, and stem cells selected by this method can be effectively used in related research and clinical fields.

6 Claims, 16 Drawing Sheets

(56) References Cited

OTHER PUBLICATIONS

Sung, et al. (2019) "Thrombin Preconditioning of Extracellular Vesicles Derived from Mesenchymal Stem Cells Accelerates Cutaneous Wound Healing by Boosting Their Biogenesis and Enriching Cargo Content.", *J. Clin. Med.*, 8, 533, pp. 1-16.
Sung, et al. (2019) "Thrombin Preconditioning Boosts Biogenesis of Extracellular Vesicles from Mesenchymal Stem Cells and Enriches Their Cargo Contents via Protease-Activated Receptor-Mediated Signaling Pathways.", *Int. J. Mol. Sci.*, 20, 2899, pp. 1-13.
Lee, et al. (2012) "Exosomes Mediate the Cytoprotective Action of Mesenchymal Stromal Cells on Hypoxia-Induced Pulmonary Hypertension." *Circulation*, 126(22): 2601-2611, (Nov. 27, 2012).

* cited by examiner

METHOD OF SELECTING STEM CELLS HAVING ABILITY TO PRODUCE EXTRACELLULAR VESICLES WITH HIGH EFFICIENCY USING ACTIVATION OF PROTEASE-ACTIVATED RECEPTOR-MEDIATED SIGNALING PATHWAYS

CROSS-REFERENCE TO RELATED APPLICATIONS

This application is a national phase application of PCT Application No. PCT/KR2020/005599, filed 28 Apr. 2020, which claims benefit of Korean Patent Application No. 10-2020-0050893, filed on 27 Apr. 2020 and Korean Patent Application No. 10-2019-0049898, filed on 29 Apr. 2019. The entire disclosures of the applications identified in this paragraph are incorporated herein by references.

FIELD

The present disclosure relates to a method of selecting stem cells having the ability to produce extracellular vesicles with high efficiency, including measuring the activity of protease-activated receptor (PAR)-mediated signaling pathways, stem cells selected using the method, and a method of screening an inducer for producing extracellular vesicles.

BACKGROUND

Extracellular vesicles (EVs) have a diameter of 40-150 nm and are secretory membrane vesicles secreted by various cells. EVs contain numerous proteins, lipids, and RNAs that are similar to those present in originating cells, and have been recognized as important messengers for cell-to-cell communication via transfer of various factors contained therein. Recent studies have shown that the therapeutic efficacy of mesenchymal stem cells (MSCs) in various disorders, such as cardiovascular diseases, lung injury, acute kidney injury, fetal hypoxic ischemic brain injury, skin wound healing, and hypoxic pulmonary hypertension, is mainly mediated by the transfer of mRNAs, microRNAs (miRNAs), and proteins via MSC-derived EVs (Circulation 2012, 126, 2601-2611.). The major advantage of therapies using MSC-derived EVs over transplantation of MSCs themselves is that EVs can overcome limitations in therapies using cells themselves. In addition, compared to MSCs, EVs can be stored without losing their biological function, and thus are more suitable for use as an "off the shelf" drug. Despite these advantages of EVs, only a small amount of EVs is secreted by MSCs, and consequently, low therapeutic efficacy is a challenge for clinical application of EVs.

In this regard, the inventors of the present disclosure confirmed in previous studies that thrombin pretreatment of MSCs exhibited the effect of increasing EV biogenesis and cargo contents thereof. However, the precise molecular mechanisms that induce the above-described effect by thrombin treatment have not yet been verified.

SUMMARY

Technical Problem

As a result of having studied and made efforts to verify via which pathway thrombin treatment in mesenchymal stem cells enhances the ability to produce extracellular vesicles, the inventors of the present disclosure specifically confirmed that thrombin treatment induced the above-described effect via protease-activated receptor (PAR)-mediated signaling pathways, and thus completed the present disclosure based on these findings.

Therefore, an object of the present disclosure is to provide a method of selecting stem cells having the ability to produce extracellular vesicles with high efficiency, the method including measuring an activation level of a protease-activated receptor (PAR)-mediated signaling pathway.

Another object of the present disclosure is to provide a stem cell having the ability to produce extracellular vesicles with high efficiency, the stem cell being selected by the above-described method.

Still another object of the present disclosure is to provide a method of screening an inducer for promoting extracellular vesicle production of stem cells, the method including:
  (a) treating stem cells with candidate materials;
  (b) measuring an activation level of a protease-activated receptor (PAR)-mediated signaling pathway; and
  (c) selecting, as an inducer for promoting extracellular vesicle production, a material that has increased the activity of the PAR-mediated signaling pathway.

However, technical problems to be solved by the present disclosure are not limited to the above-described technical problems, and other unmentioned technical problems will become apparent from the following description to those of ordinary skill in the art.

Technical Solution

According to an aspect of the present disclosure, there is provided a method of selecting a stem cell having an ability to produce extracellular vesicles with high efficiency, the method including measuring an activation level of a protease-activated receptor (PAR)-mediated signaling pathway.

The present disclosure also provides a stem cell having an ability to produce extracellular vesicles with high efficiency, the stem cell being selected by the above-described method.

The measurement of the activation level of the PAR-mediated signaling pathway may include the following processes:
  (a) culturing stem cells and then treating the stem cells with thrombin;
  (b) measuring an expression level of at least one selected from the group consisting of Ras-related protein Rab-5 (Rab-5), early endosome antigen-1 (EEA-1), phospho-extracellular signal-regulated kinase 1/2 (p-ERK1/2), and phospho-protein kinase B (p-AKT) in the thrombin-treated stem cells; and
  (c) selecting a stem cell in which the expression level has been increased, as a stem cell having an ability to produce extracellular vesicles with high efficiency.

In another embodiment of the present disclosure, the PAR may be PAR1 or PAR3.

In another embodiment of the present disclosure, the ability to produce extracellular vesicles with high efficiency may be promotion of the production of extracellular vesicles or promotion of a content of a protein in extracellular vesicles.

In another embodiment of the present disclosure, the protein may be one or more selected from the group consisting of a vascular endothelial growth factor (VEGF), a hepatocyte growth factor (HGF), angiogenin, and angiopoietin-1.

In another embodiment of the present disclosure, the stem cell may be an embryonic stem cell or an adult stem cell.

In another embodiment of the present disclosure, the adult stem cell may be one or more selected from the group consisting of a mesenchymal stem cell, a human tissue-derived mesenchymal stromal cell, a human tissue-derived mesenchymal stem cell, and a multipotent stem cell.

In another embodiment of the present disclosure, the mesenchymal stem cell may be derived from one or more tissues selected from the group consisting of an umbilical cord, umbilical cord blood, bone marrow, fat, muscle, skin, an amniotic membrane, and a placenta.

In another embodiment of the present disclosure, the thrombin may be treated at 1 U/mL to 10 U/mL.

The present disclosure also provides a method of screening an inducer for promoting extracellular vesicle production of stem cells, the method including:

(a) treating stem cells with candidate materials;
(b) measuring an activation level of a protease activated receptor (PAR)-mediated signaling pathway; and
(c) selecting, as an inducer for promoting extracellular vesicle production, a material that has increased the activity of the PAR-mediated signaling pathway.

Advantageous Effects

According to the present disclosure, when stem cells are pretreated with thrombin, the production of extracellular vesicles in the stem cells and the level of a protein in the extracellular vesicles are significantly increased via protease-activated receptor (PAR)-mediated signaling pathways, and thus stem cells having the ability to produce extracellular vesicles with high efficiency can be efficiently selected by treating stem cells with thrombin and measuring an activation level of a PAR-mediated signaling pathway, and stem cells selected by such a method can be effectively used in related research and clinical fields.

DETAILED DESCRIPTION

Figure 1A:
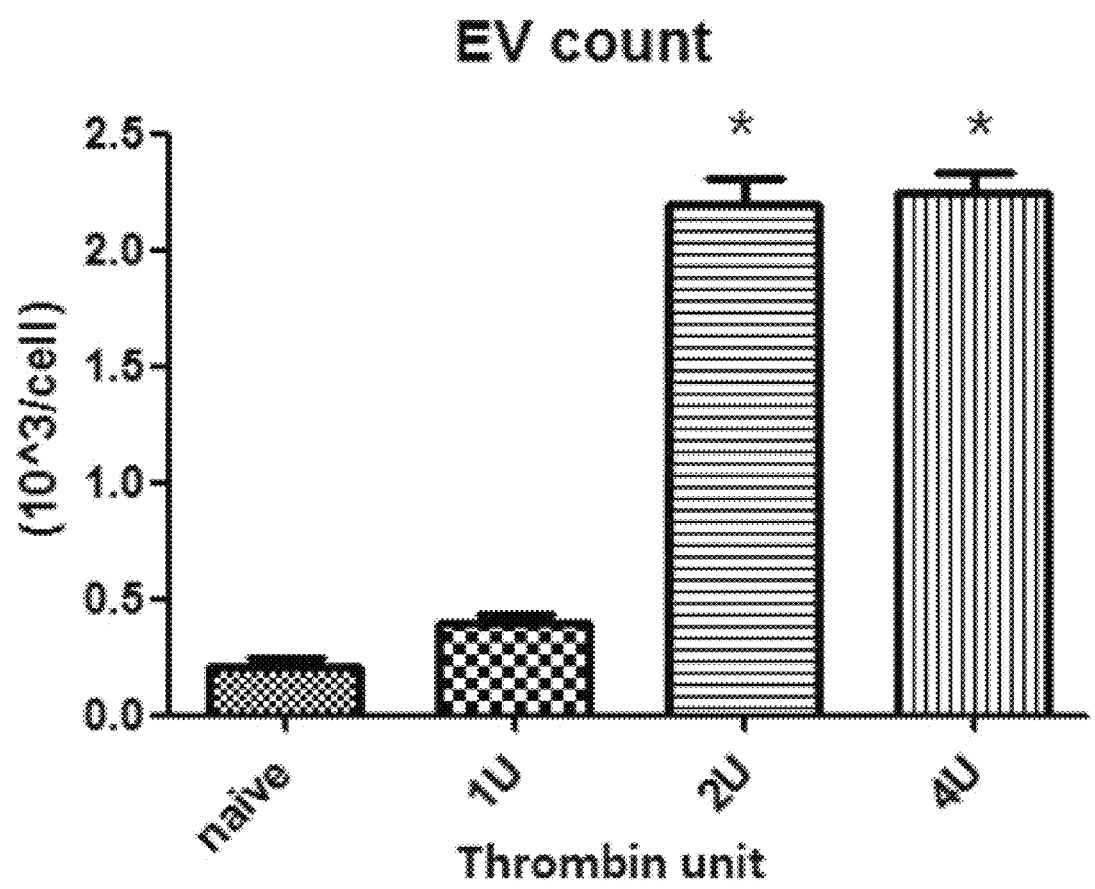
FIG. 1A illustrates the results of analyzing the level of produced extracellular vesicles in mesenchymal stem cells in a group not treated with thrombin (naive) and groups treated with thrombin at various concentrations (1 U/mL, 2 U/mL, and 4 U/mL).

As a result of having studied and made efforts to verify via which pathway thrombin treatment in mesenchymal stem cells enhances the ability to produce extracellular vesicles, the inventors of the present disclosure specifically confirmed that thrombin treatment induced the above-described effect via protease-activated receptor (PAR)-mediated signaling pathways, and thus completed the present disclosure based on these findings.

Hereinafter, the present disclosure will be described in detail.

The present disclosure provides a method of selecting a stem cell having the ability to produce extracellular vesicles with high efficiency, including measuring an activation level of a protease-activated receptor (PAR)-mediated signaling pathway.

The present disclosure also provides a stem cell having the ability to produce extracellular vesicles with high efficiency, the stem cell being selected by the above-described method.

In the present disclosure, the measurement of the activation level of the PAR-mediated signaling pathway may include: (a) culturing stem cells and then treating the stem cells with thrombin; (b) measuring an expression level of at least one selected from the group consisting of Ras-related protein Rab-5 (Rab-5), early endosome antigen-1 (EEA-1), phospho-extracellular signal-regulated kinase 1/2 (p-ERK1/2), and phospho-protein kinase B (p-AKT) in the thrombin-treated stem cells; and (c) selecting a stem cell in which the expression level has been increased, as a stem cell having the ability to produce extracellular vesicles with high efficiency.

As used herein, the term "protease-activated receptors (PAR)" refers to a subfamily of related G protein-coupled receptors that are activated by partial cleavage of the extracellular domain, and is known to be highly expressed in platelets, endothelial cells, myocytes, and neurons. There are four types of PAR: PAR1, PAR2, PAR3, and PAR4, which are classified according to the main enzymes capable of activating them. In endothelial cells, PAR is involved in regulating vascular tone and permeability, and mediates contraction, proliferation, and hypertrophy in vascular smooth muscles. PAR of endothelial cells provides a positive signal for endothelial adhesion molecules such as VCAM-1, ICAM-1, and E-selectin, is also known to contribute to inflammatory responses, and has recently been reported to be associated with muscle growth and osteogenic differentiation and proliferation. In the present disclosure, it was confirmed through specific examples that PAR mediates the ability of a stem cell to produce extracellular vesicles with high efficiency, preferably the PAR1- or PAR3-mediated signaling pathway is involved therein, and most preferably, PAR1 had a greater effect on the ability of a stem cell to produce extracellular vesicles with high efficiency than PAR3.

In a specific embodiment of the present disclosure, it was confirmed that PAR-mediated signaling pathways had a critical effect on the ability of a stem cell to produce extracellular vesicles with high efficiency.

In one embodiment of the present disclosure, the effect of thrombin pretreatment in stem cells on the production of extracellular vesicles, the levels of proteins in extracellular vesicles, and characteristics thereof was analyzed through various experiments. As a result, compared to the case in which thrombin was not treated, the amount of produced extracellular vesicles was increased 5-fold or more and the levels of proteins in extracellular vesicles were increased 2-fold or more, in proportion to the concentration of thrombin treated. It was also confirmed that thrombin treatment significantly increased the level of early endosomes in stem cells (see Example 2).

In another embodiment of the present disclosure, it was confirmed that mesenchymal stem cells expressed PAR1 and PAR3 receptors regardless of the presence or absence of thrombin treatment (see Example 3).

In another embodiment of the present disclosure, it was confirmed that, in thrombin-pretreated mesenchymal stem cells, the expression levels of early endosome markers (Rab-5 and EEA1) were significantly increased and the phosphorylation of ERK1/2 and AKT was increased (see Example 4).

In another embodiment of the present disclosure, to confirm whether PAR-mediated signaling pathways mediate thrombin treatment-induced production of extracellular vesicles, an increase in contents of proteins in extracellular vesicles, and increases in endosome markers and the phosphorylation of ERK1/2 and AKT, cells were treated with a PAR1-specific inhibitor, PAR3 siRNA, or both and analysis was performed thereon. As a result, it was confirmed that the PAR1- and PAR3-mediated signaling pathways are involved in inducing the above-described effect, and particularly, PAR1 had a more critical effect than PAR3 (see Example 5).

In process (b) above, a method of measuring the expression level may be appropriately selected by one of ordinary skill in the art from methods known in the art capable of measuring protein expression levels, and particularly, may be one or more methods selected from the group consisting of western blotting, radioimmunoassay (RIA), radioimmunodiffusion, enzyme-linked immunosorbent assay (ELISA), immunoprecipitation, flow cytometry, immunofluorescence, Ouchterlony immunodiffusion, complement fixation assay, protein chips, but the present disclosure is not limited thereto.

As used herein, the term "ability to produce extracellular vesicles with high efficiency" means an increase in the amount of extracellular vesicles produced from a stem cell and/or an increase in the level of a protein in extracellular vesicles produced from the stem cell.

The protein in extracellular vesicles may be one or more selected from the group consisting of a vascular endothelial growth factor (VEGF), a hepatocyte growth factor (HGF), angiogenin, and angiopoietin-1, but the present disclosure is not limited thereto.

In the present disclosure, "stem cell" refer to an undifferentiated cell and a cell having a self-replication ability and the ability to differentiate into two or more different types of cells.

The stem cell of the present disclosure may be an autologous or allogenic stem cell, and may be derived from any type of animal including humans and non-human mammals, and the stem cell may be derived from an adult or an embryo, but the present disclosure is not limited thereto. The stem cell of the present disclosure includes an embryonic stem cell or an adult stem cell, and is preferably an adult stem cell. The adult stem cell may be a mesenchymal stem cell, a human tissue-derived mesenchymal stromal cell, a human tissue-derived mesenchymal stem cell, or a multipotent stem cell, and is preferably a mesenchymal stem cell, but the present disclosure is not limited thereto.

The mesenchymal stem cell may be a mesenchymal stem cell derived from an umbilical cord, umbilical cord blood, bone marrow, fat, muscle, skin, an amniotic membrane, or a placenta, and preferably may be derived from umbilical cord blood, but the present disclosure is not limited thereto.

The culture of the stem cells may be appropriately selected by one of ordinary skill in the art from methods known in the art. In the present disclosure, specifically, umbilical cord blood-derived mesenchymal stem cells were cultured in an α-MEM medium, but the present disclosure is not limited thereto.

A method for thrombin treatment is not particularly limited, but preferably, thrombin may be added to a medium and stem cells may be cultured in the medium for 2 hours to 10 hours, preferably 4 hours to 8 hours, more preferably 5 hours to 7 hours, and most preferably for 6 hours. Thrombin may be included in the medium at a concentration of 1 U/ml to 10 U/ml, preferably 1 U/ml to 5 U/ml, and more preferably 2 U/ml to 4 U/ml.

According to another embodiment of the present disclosure, there is provided a method of screening an inducer for promoting extracellular vesicle production of a stem cell, the method including: (a) treating stem cells with candidate materials; (b) measuring an activation level of a protease-activated receptor (PAR)-mediated signaling pathway; and (c) selecting a material that has increased the activity of the PAR-mediated signaling pathway, as an inducer for promoting the production of extracellular vesicles.

In the present disclosure, the candidate materials may be selected from the group consisting of a compound, a microorganism culture fluid or extract, a natural substance extract, a nucleic acid, and a peptide, and the nucleic acid may be selected from the group consisting of siRNA, shRNA, microRNA, antisense RNA, an aptamer, a locked nucleic acid (LNA), a peptide nucleic acid (PNA), and a morpholino, but the present disclosure is not limited thereto.

Hereinafter, exemplary examples will be described to aid in understanding of the present disclosure. However, the following examples are merely provided to facilitate the understanding of the present disclosure and are not intended to limit the scope of the present disclosure.

EXAMPLES

Example 1. Experimental Preparation and Experimental Methods 1-1. Culture and Pretreatment of Mesenchymal Stem Cells Human umbilical cord blood-derived mesenchymal stem cells (MSCs) were purchased from Medipost Co., Ltd. (Seoul, Korea) and were used in this study. The cells were isolated from a single donor with informed consent and manufactured in strict compliance with good manufacturing processes at passage 6. It was confirmed that the mesenchymal stem cells expressed CD105 (99.6%) and CD73 (96.3%), and did not express CD34 (0.1%), CD45 (0.2%), or CD14 (0.1%), and it was also confirmed that the cells were positive for human leukocyte antigen (HLA)-AB (96.8%) and not positive for HLA-DR (0.1%).

To pretreat the umbilical cord blood-derived mesenchymal stem cells with thrombin, first, the mesenchymal stem cells were cultured in α-MEM (Gibco, Grand Island, NY, USA) supplemented with 10% (v/v) fetal bovine serum (FBS, Gibco), 100 units/mL penicillin, and 100 µg/mL streptomycin (Invitrogen, Carlsbad, CA, USA) under standard culture conditions. When the cells reached approximately 90% confluency in a culture plate, the cells were washed three times with phosphate buffered saline (PBS) to remove contaminated FBS-derived exosomes, and were then incubated in new serum-free α-MEM supplemented with human recombinant thrombin (1 U/mL, 2 U/mL, and 4 U/mL; Sigma-Aldrich, St. Louis, MO, USA) for 6 hours. After the medium was collected, about 2×106 cells per 100 mm culture dish was counted using a Luna-FL™ system (Logos Biosystems, Anyang-si, Korea).

1-2. Isolation and Quantification of Extracellular Vesicles (EVs)

To isolate extracellular vesicles (hereinafter, referred to as EVs) secreted by the umbilical cord blood-derived mesenchymal stem cells pretreated with thrombin according to the method of Example 1-1, an experiment was conducted according to the following processes. Specifically, the above recovered medium was centrifuged at 3,000 rpm and 4° C. for 30 minutes to remove cell debris, and then centrifuged at 100,000 rpm and 4° C. for 120 minutes to precipitate EVs. Then, the precipitated pellet was washed twice, re-suspended in sterile PBS, and stored at −80° C. until use.

The distribution of EVs was analyzed by measuring the rate of Brownian motion using NanoSight (NanoSight NS300; Malvern, Worcestershire, UK), which is equipped with fast video capture and particle-tracking software. The obtained EVs were re-suspended in PBS (500 µl, 1 mg/mL total protein), and size and polydispersity thereof were measured. In addition, to quantify the production of EVs by a single cell, cells were counted using a LUNA-FL system according to the manufacturer's protocol using the medium recovered above. The number of EVs produced by a single cell was calculated by dividing the total number of EVs by the number of cells.

1-3. Observation Through Transmission Electron Microscope (TEM) and Scanning Electron Microscope (SEM)

EVs (5 µl) were fixed with 2% glutaraldehyde, loaded on 200-mesh formvar/carbon-coated electron microscopy grids (Electron Microscopy Sciences, Washington, PA, USA), and incubated for 10 minutes. Subsequently, the EVs were washed with filtered distilled water and stained with 2% uranyl acetate in water for 1 minute. Thereafter, the stained EVs were observed using a Tecnai Spirit G2 transmission electron microscope (FEI, Hillsboro, OR, USA) operating at 120 kV, and then an image thereof was acquired.

Meanwhile, to observe isolated EVs using a scanning electron microscope, EVs were fixed in 2.5% glutaraldehyde and loaded on a polycarbonate membrane. Next, the membrane was washed once with PBS and water and then dehydrated with acetone. Subsequently, the acetone was removed by critical point drying using liquid carbon dioxide. Samples were mounted on aluminum stubs with carbon tape and mounted on an SEM stub. After sputter coating with 3-5 nm platinum, the samples were observed using a scanning electron microscope (Zeiss Auriga Workstation, Oberkochen, Germany) and images thereof were acquired.

1-4. PAR1-Specific Inhibitor Treatment and PAR3 Knockdown

The selective PAR1 antagonist SCH79797 (N3-cyclopropyl-7-[[4-(1-methylethyl)phenyl]methyl]-7H-pyrrolo[3,2-f]quinazolin-1,3-diamine dihydrochloride) was obtained from Tocris (Bristol, UK). Subsequently, to treat umbilical cord blood-derived mesenchymal stem cells with the above material, the SCH79797 was added to a culture medium at a concentration of 1 µM 1 hour before thrombin treatment.

Meanwhile, to knock down PAR3, mesenchymal stem cells were transfected with RAR3-targeting siRNA using a Lipofectamine® RNAiMAX transfection reagent (Invitrogen, Carlsbad, CA, USA) according to the manufacturer's protocol. At this time, mesenchymal stem cells were treated with scrambled siRNA as a negative control using the same method and under the same conditions. Control siRNA and PAR3 siRNA were purchased from Santa Cruz Biotechnology (Santa Cruz, CA, USA).

1-5. Early Endosome Labeling

Early endosomes were labeled using CellLight® reagent-green fluorescent protein (GFP), BacMam 2.0 (Thermo Fisher Scientific, San Jose, CA, USA) according to the manufacturer's instructions. Briefly, mesenchymal stem cells were dispensed in a 12-well plate at a density of 1.5×104 per well, and after cells were attached, BacMam 2.0 reagent was added at a concentration of 40 particles per cell (PPC). Next, to measure Rab5α-GFP expression, early endosomes were labeled using CellLight® early endosomes-GFP, BacMam 2.0. Thereafter, to estimate the number of GFP-labeled endosomes, the optical density of green immunofluorescence was measured using ImageJ (National Institutes of Health, Bethesda, MD, USA).

1-6. Bioplex Assay

To analyze the cytokine levels of EVs by ELISA, an experiment was conducted using the following method. Specifically, a homogenate of isolated EVs was added to a well containing 0.1 mL of lysis buffer in an ELISA kit. Subsequently, proteins in EVs were quantified using the Bradford method, and then 1 μg of protein was loaded into each well. Thereafter, the levels of angiogenin, angiopoietin-1, VEGF, and HGF, which are present in EVs, were quantified using the Fluorokine® MAP Human Angiogenesis Custom Premix Kit A (R & D Systems, Minneapolis, MN, USA).

1-7. Immunoblot Analysis

Umbilical cord blood-derived mesenchymal stem cells and EVs were lysed by adding an equal volume of RIPA buffer (Sigma-Aldrich, St. Louis, MO, USA). The protein contents of the lysates were quantified using the Bradford method, and samples containing 10 μg of proteins were mixed with loading buffer containing β-mercaptoethanol, boiled for 10 minutes, and separated according to size by 12% SDS-polyacrylamide gel electrophoresis (SDS-PAGE). Subsequently, the separated proteins were transferred to nitrocellulose membranes, and then a 5% bovine serum albumin (BSA) solution was prepared with 0.5% Tween-20-containing 1×PBS-T, the membranes were blocked therewith at room temperature, followed by treatment with primary antibodies and incubation at room temperature for 1 hour. After incubation, the membranes were washed with 1×PBS-T, followed by incubation with anti-mouse or anti-rabbit horseradish peroxidase-conjugated immunoglobulin G (1:2000) secondary antibodies while being stirred at room temperature for 1 hour. Subsequently, after washing with PBS-T, protein bands were detected using an ECL Select chemiluminescence reagent (GE Healthcare Life Sciences, Piscataway, NJ, USA), and band images were acquired with X-ray films.

1-8. Statistical Analysis

All quantitative results were obtained from three repeated experimental results. Data was expressed as mean±standard deviation (SD), and statistical analyses were carried out using two-sample t-tests to compare two groups and one-way analysis of variance (ANOVA) for three groups. A p value less than 0.05 was considered statistically significant.

Example 2. Analysis of Effect of Thrombin Pretreatment on Synthesis of EVs, Protein Levels, and Characteristics of EVs The inventors of the present disclosure conducted the following experiments to analyze the effect of thrombin pretreatment in mesenchymal stem cells on the synthesis of EVs, the levels of proteins present in EVs, and the characteristics of EVs.

2-1. Analysis of Production of EVs and Protein Levels

First, mesenchymal stem cells were treated with thrombin at various concentrations of 1-4 U/mL using the method of Example 1-1, and the amount of EVs was analyzed according to the method of Example 1-2. As a result, as illustrated in FIG. 1A, the production of EVs was increased in a thrombin concentration-dependent manner, and was significantly increased particularly at concentrations of 2 U/mL and 4 U/mL.

Figure 1B:
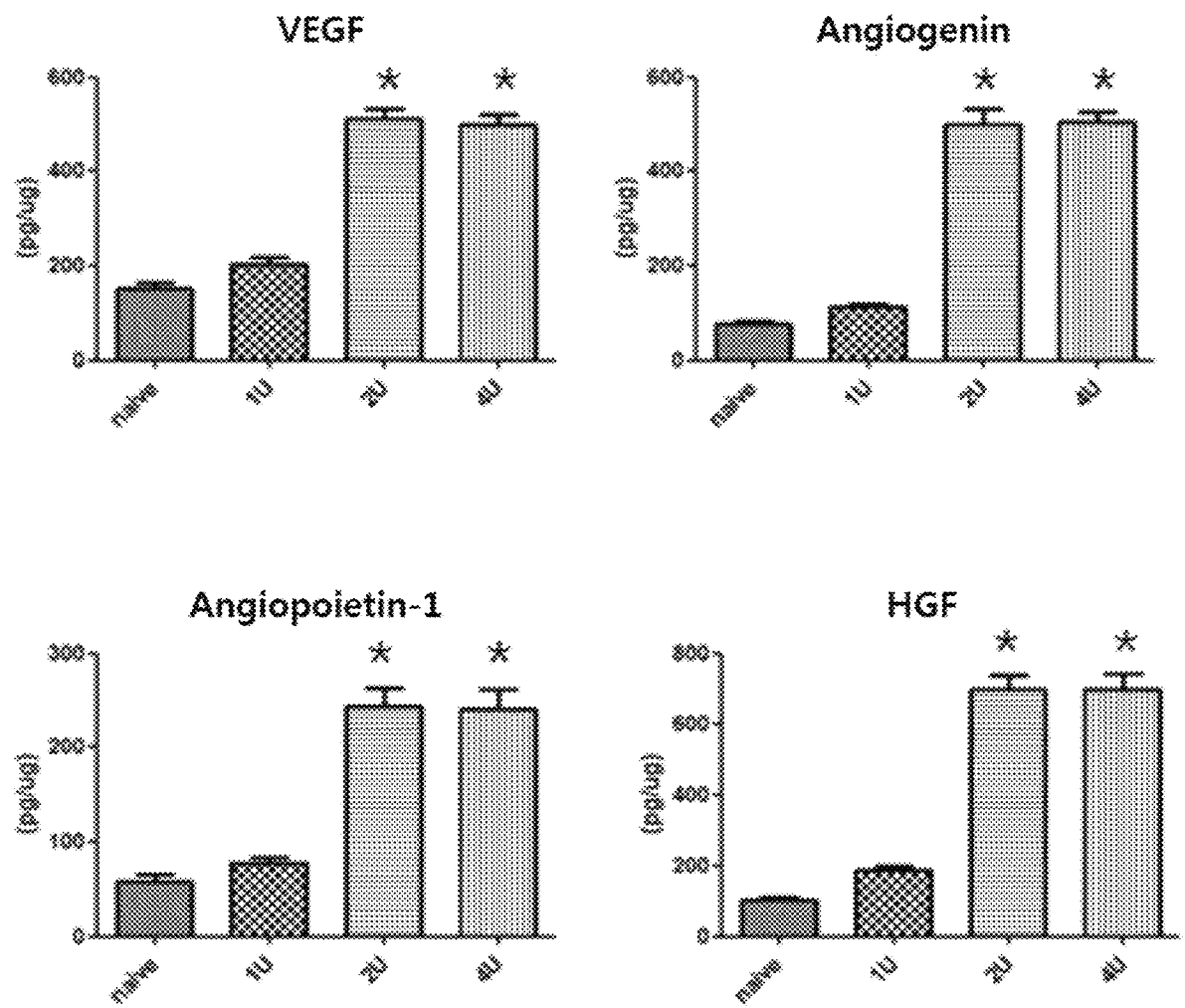
FIG. 1B illustrates the results of analyzing the levels of proteins (VEGF, Angiogenin, Angiopoietin-1, and HGF) contained inside extracellular vesicles in mesenchymal stem cells in a group not treated with thrombin (naive) and groups treated with thrombin at various concentrations (1 U/mL, 2 U/mL, and 4 U/mL).

In addition, as a result of analyzing the levels of proteins in EVs, as illustrated in FIG. 1B, it was confirmed that, compared to mesenchymal stem cells not treated with thrombin, the levels of a vascular endothelial growth factor (VEGF), angiogenin, angiopoietin-1, and a hepatocyte growth factor (HGF) were significantly increased in groups treated with thrombin at 2 U/mL and 4 U/mL, respectively. Furthermore, based on the above results, 2 U/mL was selected as the optimum treatment concentration of human thrombin and subsequent experiments were conducted.

2-2. Early Endosome Analysis

Figure 1C:
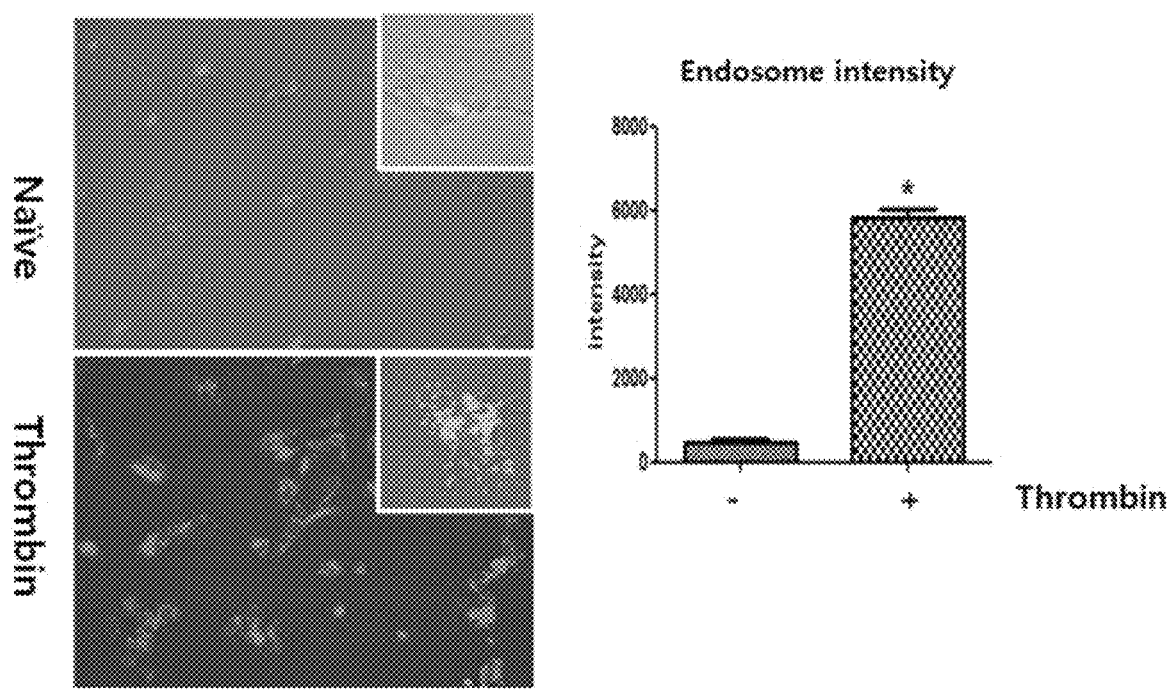
FIG. 1C illustrates fluorescent images and quantitative results obtained by analyzing the difference in early endosomes according to the presence or absence of thrombin treatment after early endosomes in mesenchymal stem cells were labeled with GFP.

The inventors of the present disclosure labeled early endosomes in the stem cells using a CellLight Early Endosomes-GFP kit and compared mesenchymal stem cells not treated with thrombin (Naive) and thrombin-pretreated mesenchymal stem cells (Thrombin). Specifically, as a result of comparing the difference between endosomes of the two groups of cells through the fluorescence images and quantitative results thereof, as illustrated in FIG. 1C, a significantly high level of early endosomes was observed in the thrombin-pretreated stem cells.

2-3. Observation of EVs Through Electron Microscopes

Figure 1D:
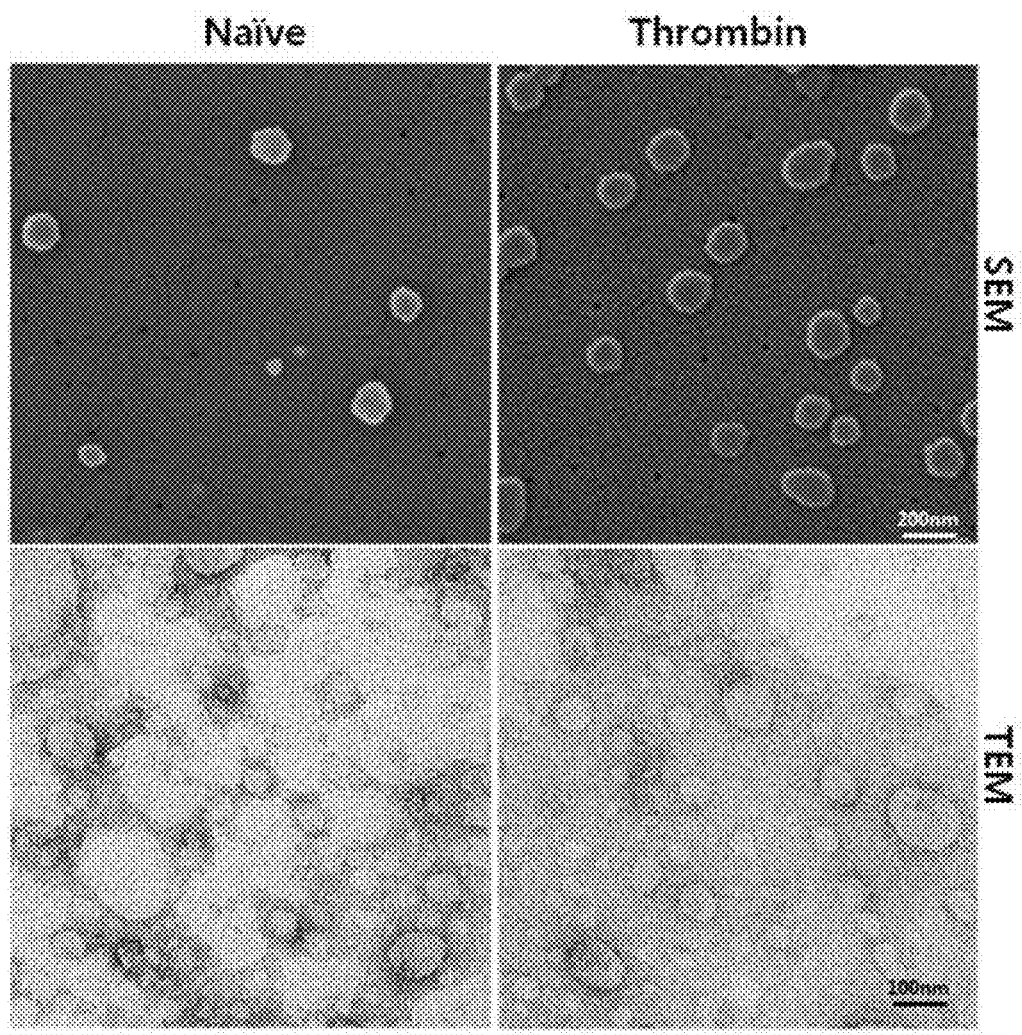
FIG. 1D illustrates the results of observing, using a scanning electron microscope (SEM) and a transmission electron microscope (TEM), extracellular vesicles isolated from mesenchymal stem cells not treated with thrombin (naive) and mesenchymal stem cells pretreated with thrombin, respectively.

In addition, to compare the difference between EVs according to thrombin pretreatment, isolated EVs were observed using a scanning electron microscope and a transmission electron microscope according to the method of Example 1-3. As a result, as illustrated in FIG. 1D, compared to the mesenchymal stem cells not treated with thrombin, more EVs were observed in the thrombin-pretreated mesenchymal stem cells.

2-4. Characterization of EVs

Figure 1E:
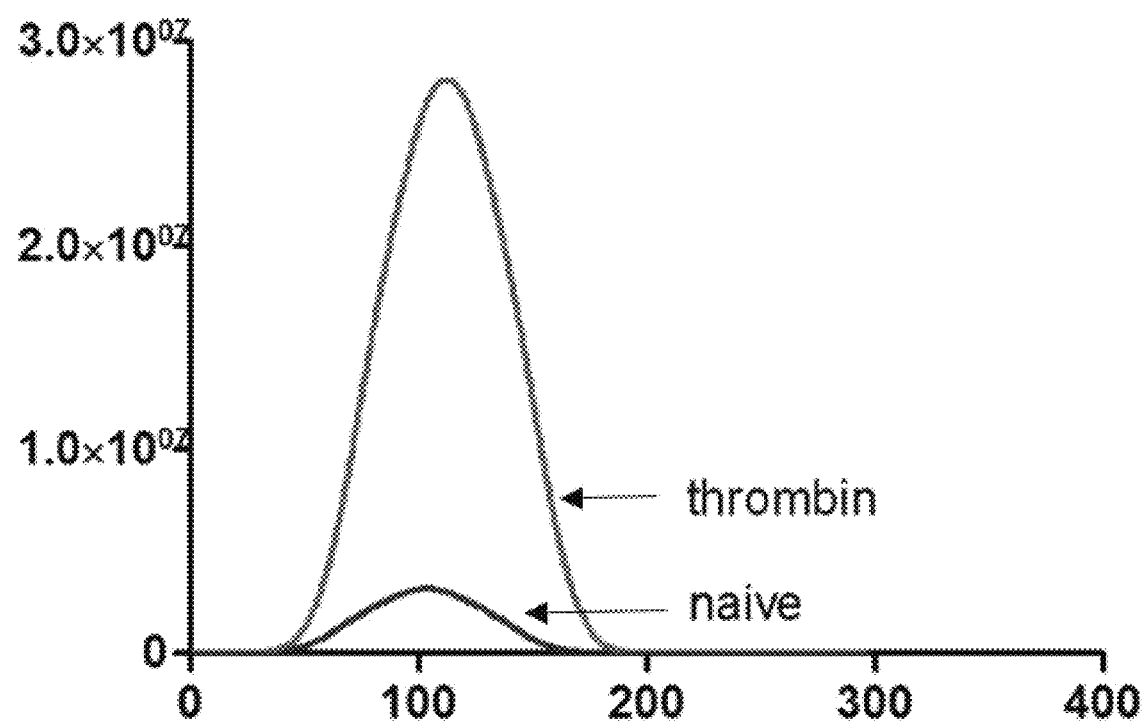
FIG. 1E illustrates the results of measuring the diameter and number of extracellular vesicles isolated from each of the same groups as those of FIG. 1D.

The sizes of EVs isolated from mesenchymal stem cells not treated with thrombin and thrombin-pretreated mesenchymal stem cells, respectively, were measured. As a result, it was confirmed as illustrated in FIG. 1E that both cases exhibited a peak at 100 nm and the sizes of EVs isolated from the respective groups of cells were identical to each other. However, a greater number of isolated EVs was confirmed in the thrombin-pretreated mesenchymal stem cells.

Figure 1F:
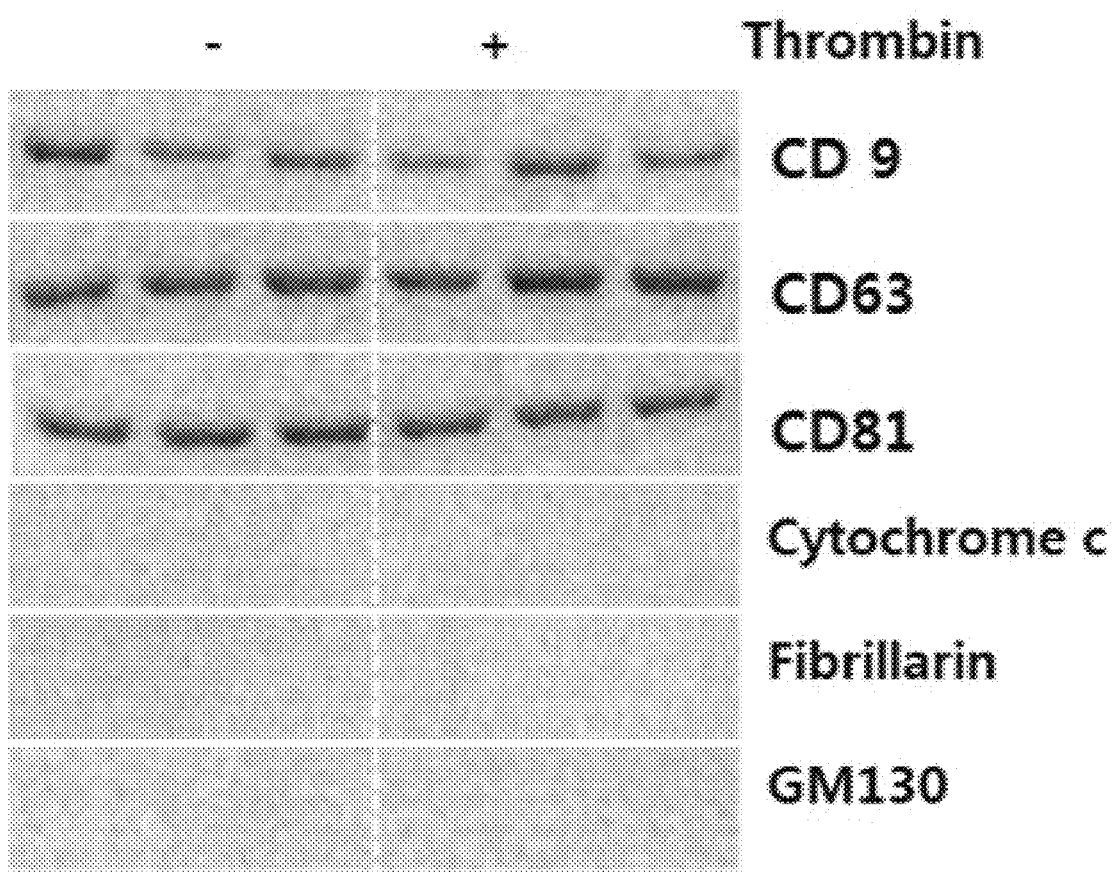
FIG. 1F illustrates the results of confirming, through immunoblotting analysis, whether or not the exosome-specific markers CD9, CD63, and CD81, the mitochondria marker cytochrome c, the nuclear marker fibrillarin, and the Golgi body marker GM130 were expressed in extracellular vesicles isolated from each of the same groups as those of FIG. 1D.

In addition, the expression levels of various markers were analyzed by immunoblotting of EVs isolated from the two cases of mesenchymal stem cells. As a result, it was confirmed as illustrated in FIG. 1F that, regardless of the presence or absence of thrombin treatment, all the EVs expressed the exosome-specific markers CD9, CD63, and CD81, and did not express the mitochondria marker cytochrome c, the nuclear marker fibrillarin, and the Golgi body marker GM130.

Example 3. Confirmation of PAR Expression of Mesenchymal Stem Cells

Figure 2A:
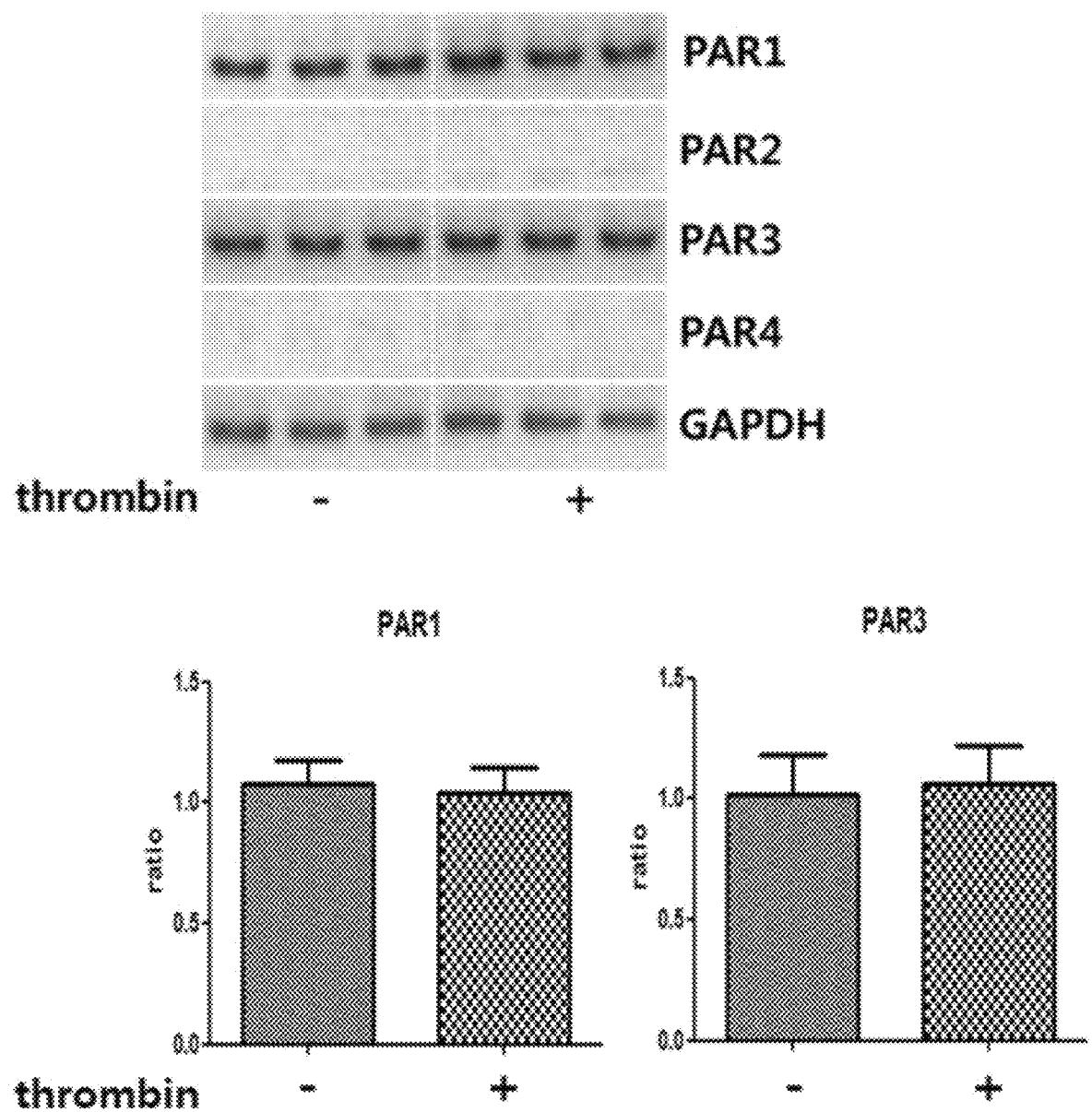
FIG. 2A illustrates the results of measuring the expression levels of PAR1, PAR2, PAR3, and PAR4 and the quantitative results of PAR1 and PAR3 in mesenchymal stem cells not treated with thrombin and mesenchymal stem cells pretreated with thrombin.

Based on the results of Example 2, the inventors of the present disclosure performed immunoblotting analysis according to the method of Example 1-7 to determine whether mesenchymal stem cells express receptors for thrombin. Specifically, the expression levels of the PAR1, PAR2, PAR3, and PAR4 proteins were analyzed for each of the cases of mesenchymal stem cells not treated with thrombin and thrombin-pretreated mesenchymal stem cells. As a result, it was confirmed as illustrated in FIG. 2A that the mesenchymal stem cells expressed PAR1 and PAR3 and did not express PAR2 and PAR4 regardless of the presence or absence of thrombin treatment. This suggests that thrombin pretreatment can affect mesenchymal stem cells via PAR1 and PAR3.

Figure 2B:
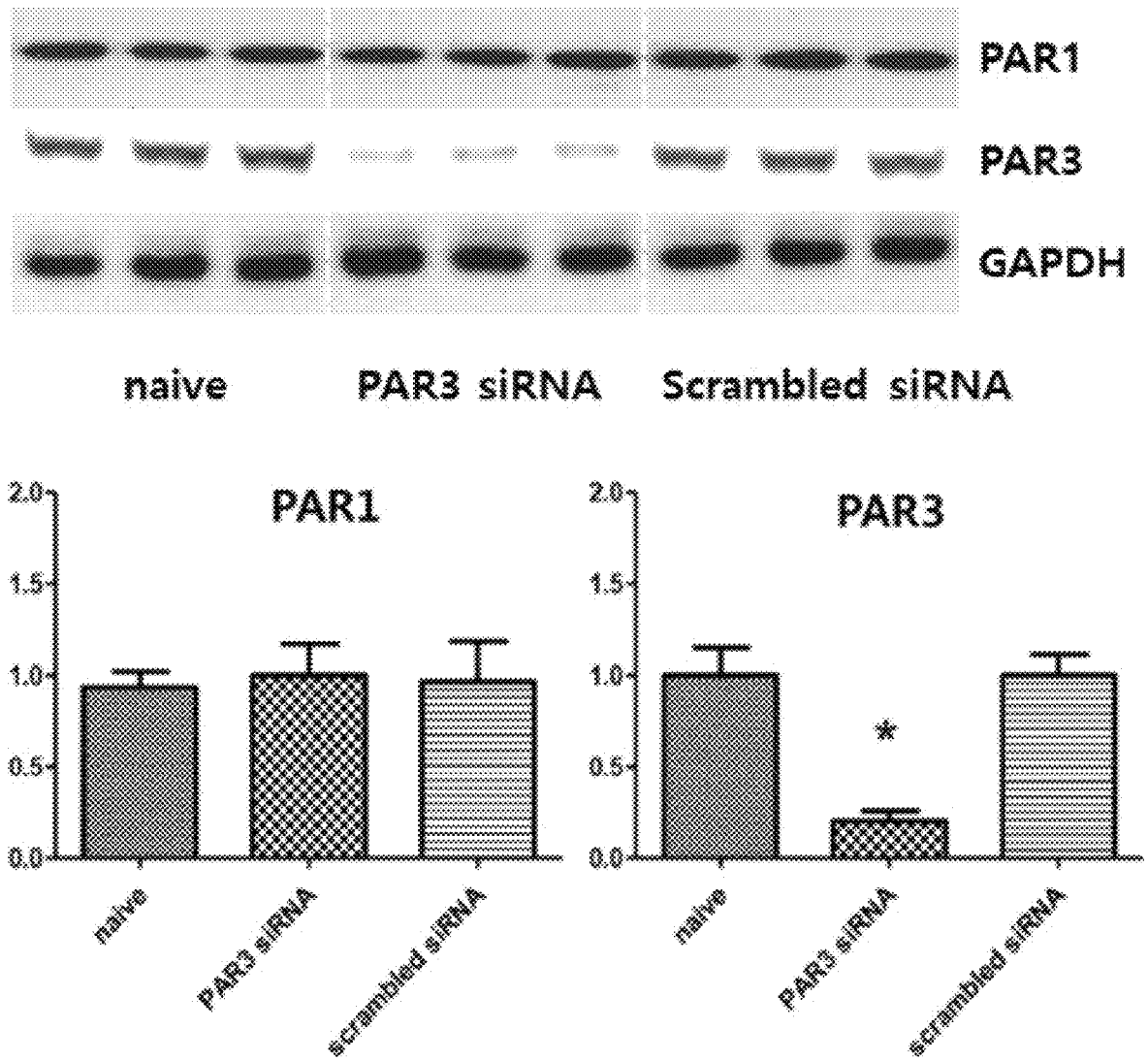
FIG. 2B illustrates the results of measuring PAR1 and PAR3 expression levels and quantitative results thereof in mesenchymal stem cells in a group not treated with thrombin (naive), a group treated with PAR3-specific siRNA (PAR3 siRNA), and a group treated with siRNA as a control (scrambled siRNA).

Furthermore, it was examined whether or not PAR3-specific siRNA (PAR3 siRNA) specifically inhibits the expression of PAR3. To this end, the mesenchymal stem cells were transfected with control siRNA (scrambled siRNA) and subjected to immunoblotting analysis. As a result, it was confirmed as shown in FIG. 2B that, in the case of treatment with PAR3 siRNA, the expression level of PAR1 was not changed and only the expression of PAR3 was specifically inhibited, whereas, in the case of treatment with control siRNA, no change was shown in the expression levels of both PAR1 and PAR3. Through this, it can be seen that PAR3 siRNA used in the present example specifically inhibits only the expression of PAR3.

Figure 3A:
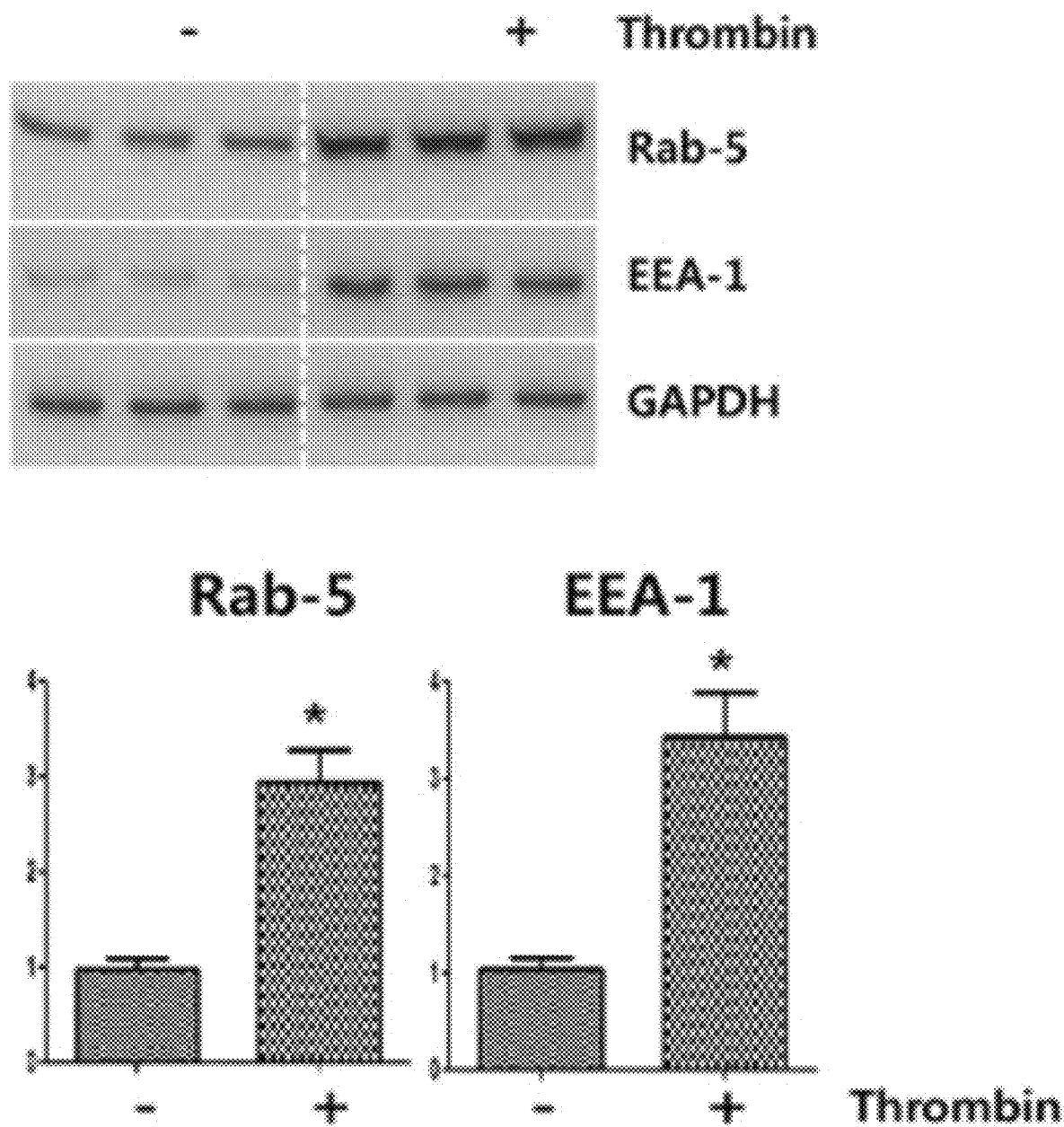
FIG. 3A illustrates measurement results showing the expression levels of endosome markers (Rab-5 and EEA-1) according to the presence or absence of thrombin treatment in mesenchymal stem cells.

Example 4. Confirmation of Increases in Early Endosome Marker Protein Levels and Phosphorylation of ERK1/2 and AKT Pathways by Thrombin Pretreatment Based on the results of Example 2, the inventors of the present disclosure analyzed a change in the expression levels of early endosome markers (Rab-5 and EEA-1) by immunoblotting according to the presence or absence of thrombin pretreatment. As a result, it was confirmed as shown in FIG. 3A that, upon treatment with thrombin, the expression levels of the early endosome markers Rab-5 and EEA-1 were significantly increased.

Figure 3B:
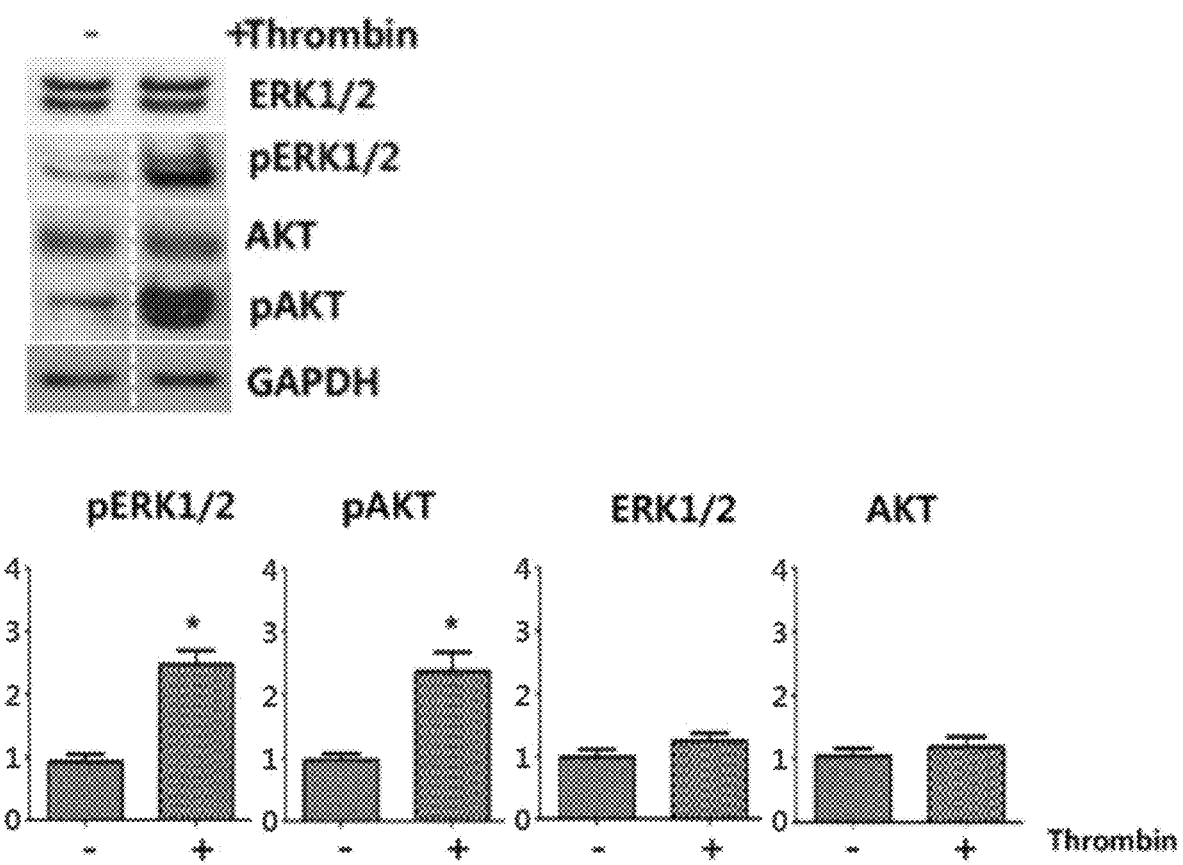
FIG. 3B illustrates measurement results showing the expression levels of ERK1/2, AKT, and phosphorylated forms thereof, i.e., the pERK1/2 and pAKT proteins, according to the presence or absence of thrombin treatment in mesenchymal stem cells.

In addition, to examine whether the ERK1/2 and AKT signaling pathways are activated in the mesenchymal stem cells according to the present disclosure according to the presence or absence of thrombin treatment, the phosphorylation levels of ERK1/2 and AKT were analyzed. As a result, it was confirmed as shown in FIG. 3B that, compared to the mesenchymal stem cells not treated with thrombin, the expression of the pERK1/2 and pAKT proteins was significantly increased in the thrombin-pretreated mesenchymal stem cells. In addition, in the case of non-phosphorylated forms of ERK1/2 and AKT, although not statistically significant, expression tended to increase slightly by thrombin treatment.

Figure 4A:
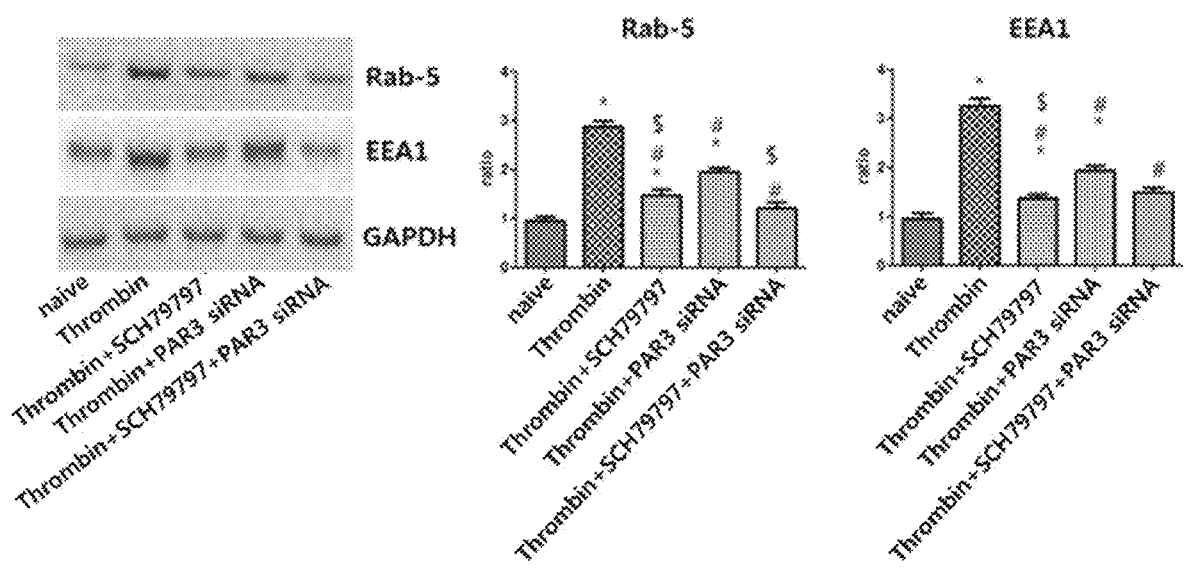
FIG. 4A illustrates the results of analyzing the expression levels of endosome markers (Rab-5 and EEA-1) in mesenchymal stem cells in a group not treated with thrombin (naive), a group pretreated with thrombin (Thrombin), a group pretreated with thrombin and then treated with the PAR1-specific inhibitor SCH79797 (Thrombin+SCH79797), a group pretreated with thrombin and then treated with PAR3-specific siRNA (Thrombin+PAR3 siRNA), and a group pretreated with thrombin and then treated with both SCH79797 and PAR3 siRNA (Thrombin+SCH79797+PAR3 siRNA).

Example 5. Confirmation of Inhibition of Rab-5 and EEA1 Expression, ERK1/2 and AKT Phosphorylation, and EV Production by PAR Inhibition 5-1. Confirmation of Inhibition of Rab-5 and EEA1 Expression and ERK1/2 and AKT Phosphorylation To examine how thrombin induces the expression of the early endosome markers Rab-5 and EEA-1, the inventors of the present disclosure treated thrombin-pretreated mesenchymal stem cells with the PAR1-specific antagonist SCH79797, transfected the stem cells with PAR3-specific siRNA, or treated the stem cells with both materials, and then respectively analyzed the expression levels of Rab-5 and EEA-1. As a result, it was shown as illustrated in FIG. 4A that the expression levels of Rab-5 and EEA-1 were significantly reduced in both the group treated with SCH79797 (Thrombin+SCH79797) and the group treated with PAR3 siRNA (Thrombin+PAR3 siRNA) compared to the group pretreated with thrombin alone (Thrombin). At this time, it was shown that the expression levels were further reduced in the SCH79797-treated group compared to the PAR3 siRNA-treated group. In addition, it was confirmed that the expression level of each protein was the most reduced in the group co-treated with SCH79797 and PAR3 siRNA (Thrombin+SCH79797+PAR3 siRNA).

Figure 4B:
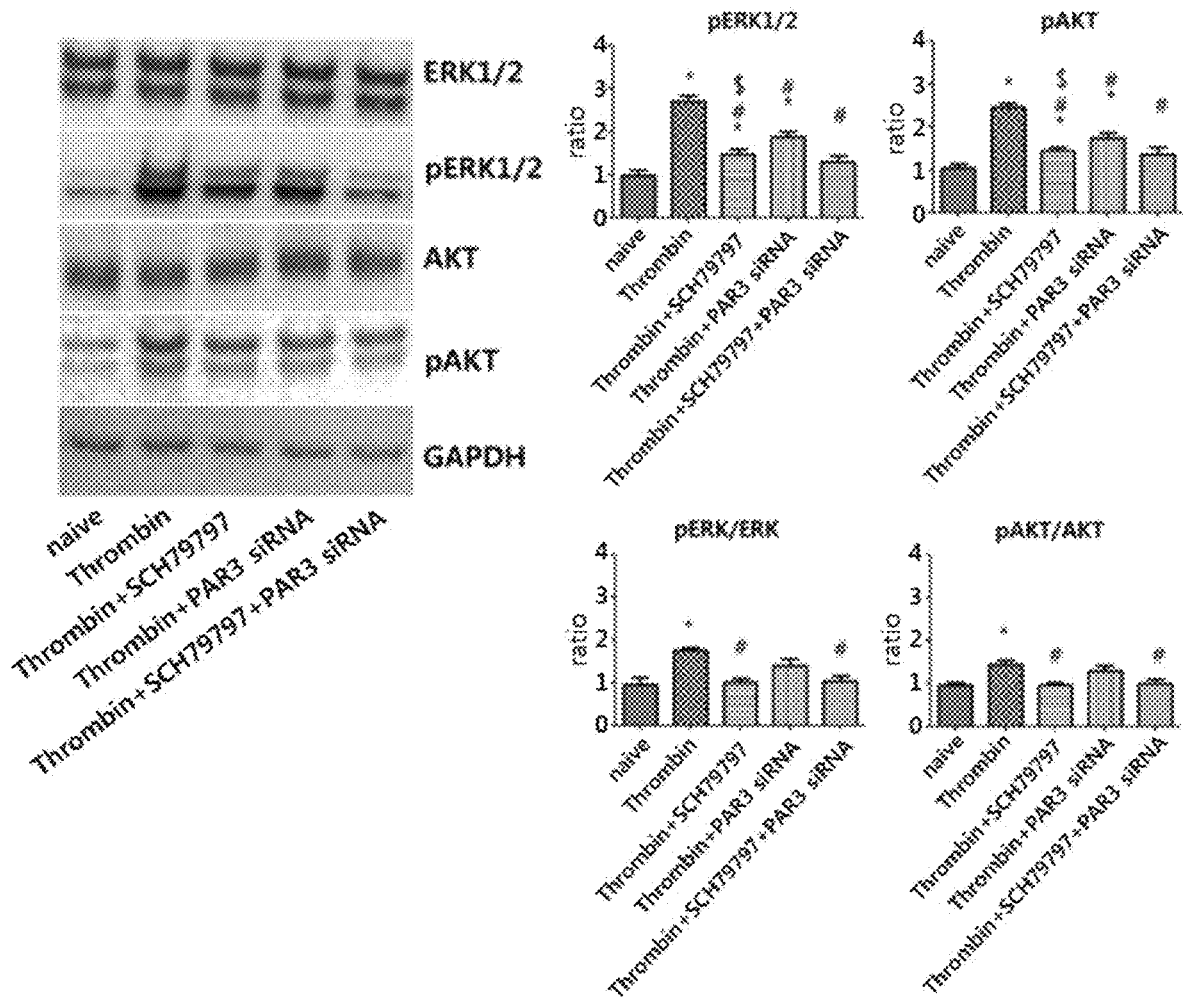
FIG. 4B illustrates the results of analyzing the expression levels of the pERK1/2, pAKT, ERK1/2, and AKT proteins in each of the same groups as those of FIG. 4A.

In addition, to examine how thrombin induces the activation of the ERK1/2 and AKT pathways, thrombin-pretreated mesenchymal stem cells were treated with SCH79797- and/or PAR-3-specific siRNA. As a result, as can be seen in FIG. 4B, an increase in the phosphorylation of ERK1/2 and AKT by thrombin pretreatment was significantly inhibited in the groups respectively treated with SCH79797 and PAR3 siRNA, and was inhibited at a more significant level upon treatment with SCH79797 than upon treatment with PAR-3-specific siRNA. Moreover, it was confirmed that, upon co-treatment with both materials, the increase was most significantly inhibited. These results suggest that PAR-1 signaling is more involved in the activation of Rab-5, EEA-1, ERK1/2, and AKT by thrombin pretreatment, whereas PAR-3 signaling is partially involved therein.

5-2. Confirmation of Inhibition of Production of EVs and Increase in Protein Levels Inside EVs To determine whether the production of EVs in mesenchymal stem cells is regulated by PAR, thrombin-pretreated mesenchymal stem cells were transfected with the PAR1-specific antagonist SCH79797 and/or PAR3-specific siRNA.

Figure 5A:
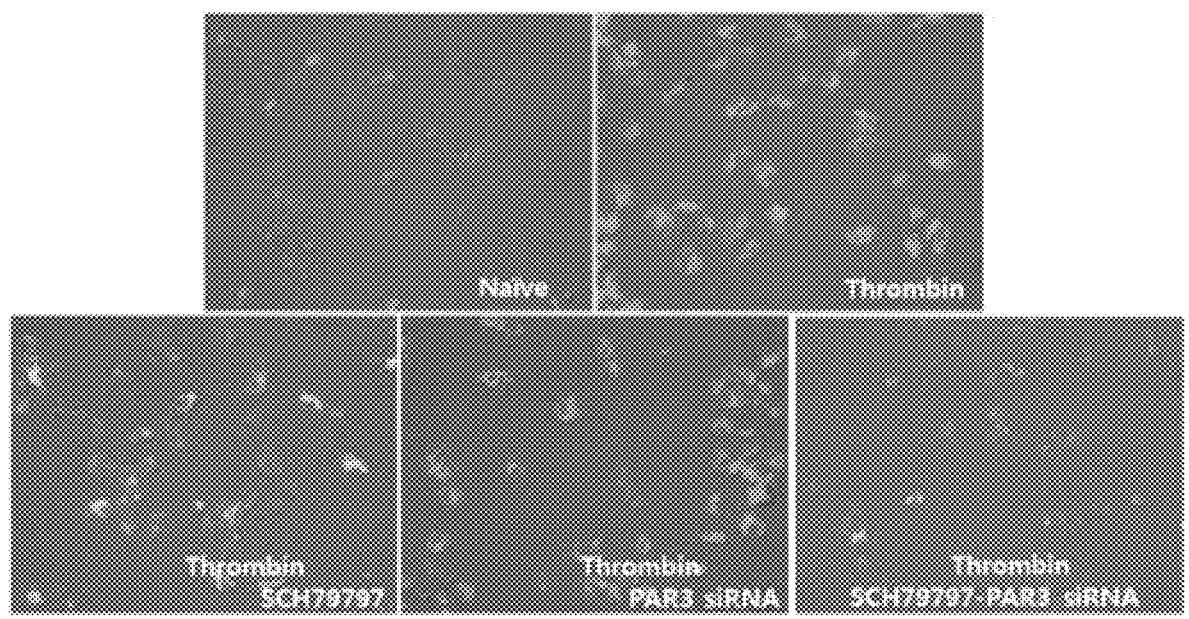
FIG. 5A illustrates fluorescent images and quantitative results thereof obtained by measuring the number of endosomes in each of the same groups as those of FIG. 4A after endosomes in mesenchymal stem cells were labeled with GFP and the nuclei were stained with DAPI.

First, to compare early endosomes in a control and experimental groups, after thrombin pretreatment, endosomes were labeled with green fluorescence using a Cell-Light Early Endosomes-GFP kit. Thereafter, as a result of analyzing fluorescence images and quantitative results thereof, as illustrated in FIG. 5A, an increase in the number of early endosomes by thrombin treatment was significantly inhibited in the groups respectively treated with SCH79797 and PAR3 siRNA. It was also confirmed that the increase was more significantly inhibited by SCH79797 treatment rather than transfection with PAR3 siRNA, and was inhibited at the highest level in the case of co-treatment with SCH79797 and PAR3 siRNA.

Figure 5B:
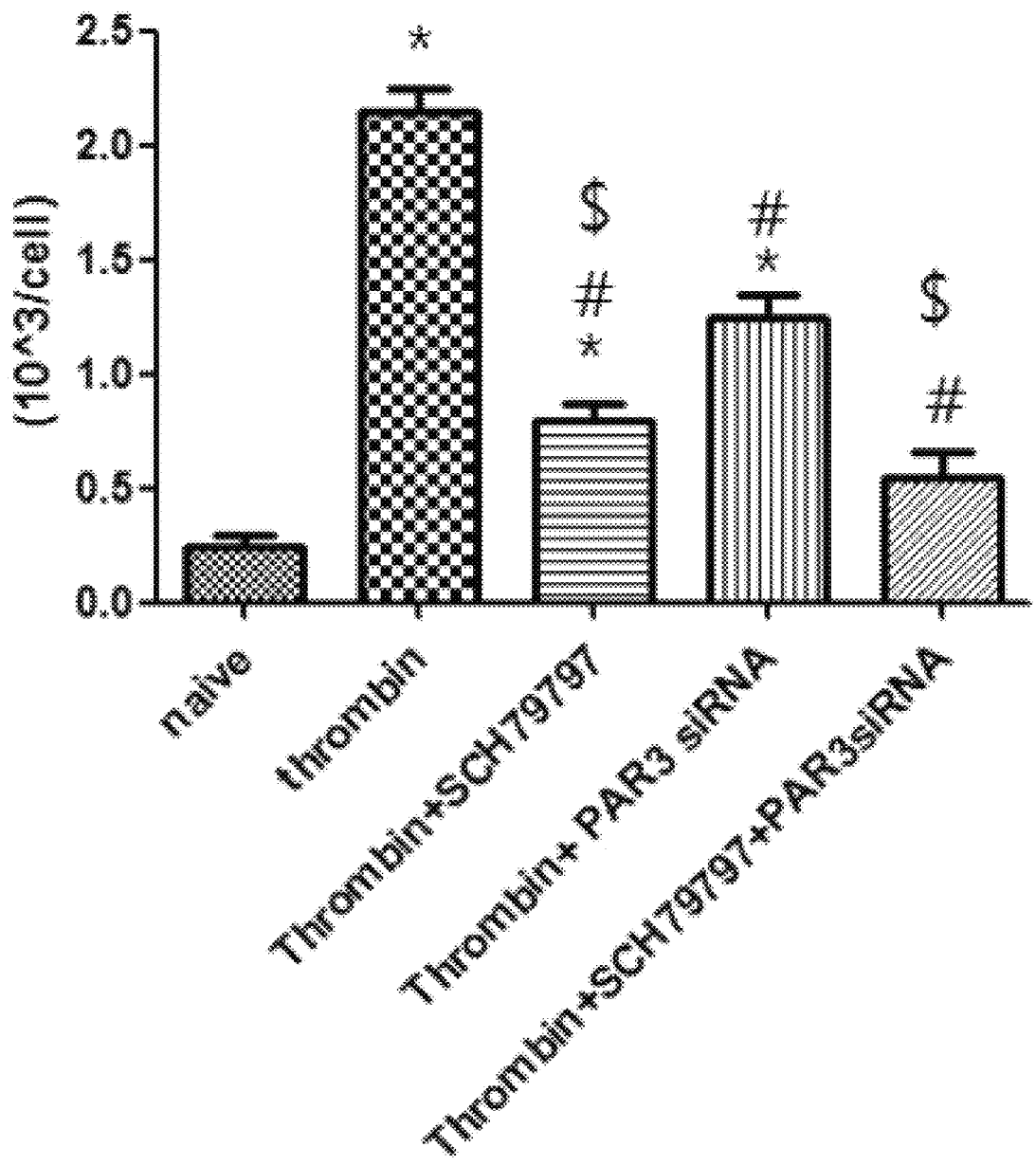
FIG. 5B illustrates the results of measuring the number of extracellular vesicles in each of the same groups as those of FIG. 4A.
Figure 5C:
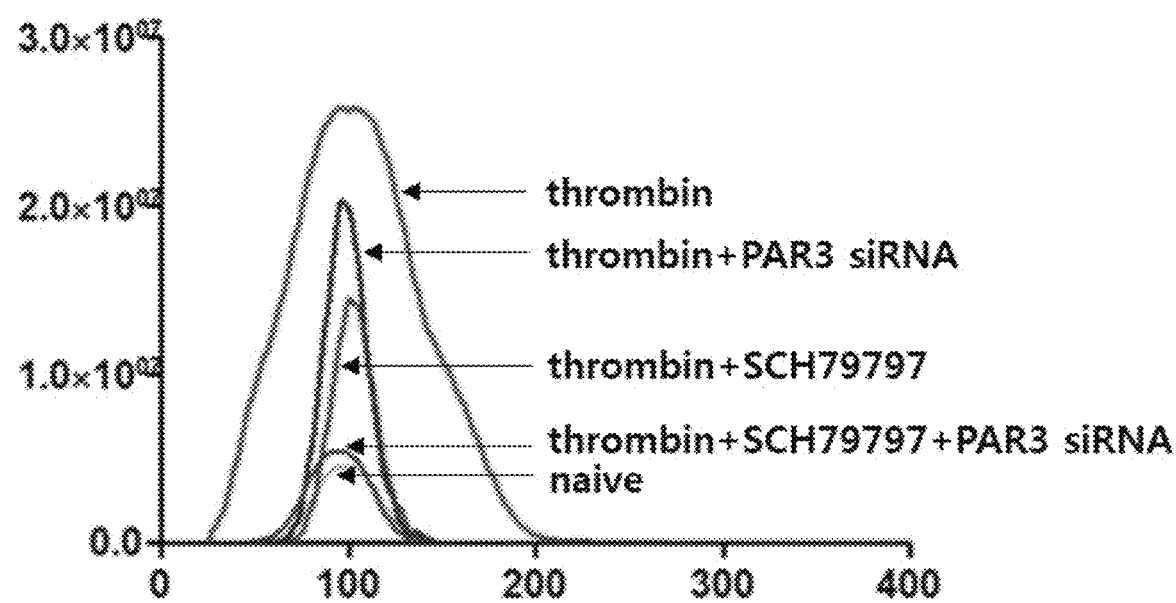
FIG. 5C illustrates the results of measuring the size and number distribution of extracellular vesicles in each of the same groups as those of FIG. 4A.

Furthermore, increases in the number of extracellular vesicles in umbilical cord blood-derived mesenchymal stem cell culture media of the same groups as described above were compared. As a result, it was confirmed as shown in FIGS. 5B and 5C that the increase in the number of extracellular vesicles by thrombin treatment was significantly inhibited in the groups respectively treated with SCH79797 and PAR3 siRNA, was inhibited at a higher level in the case of SCH79797 treatment than in the case of transfection with PAR3 siRNA, and was inhibited at the highest level in the case of co-treatment with both materials.

Figure 5D:
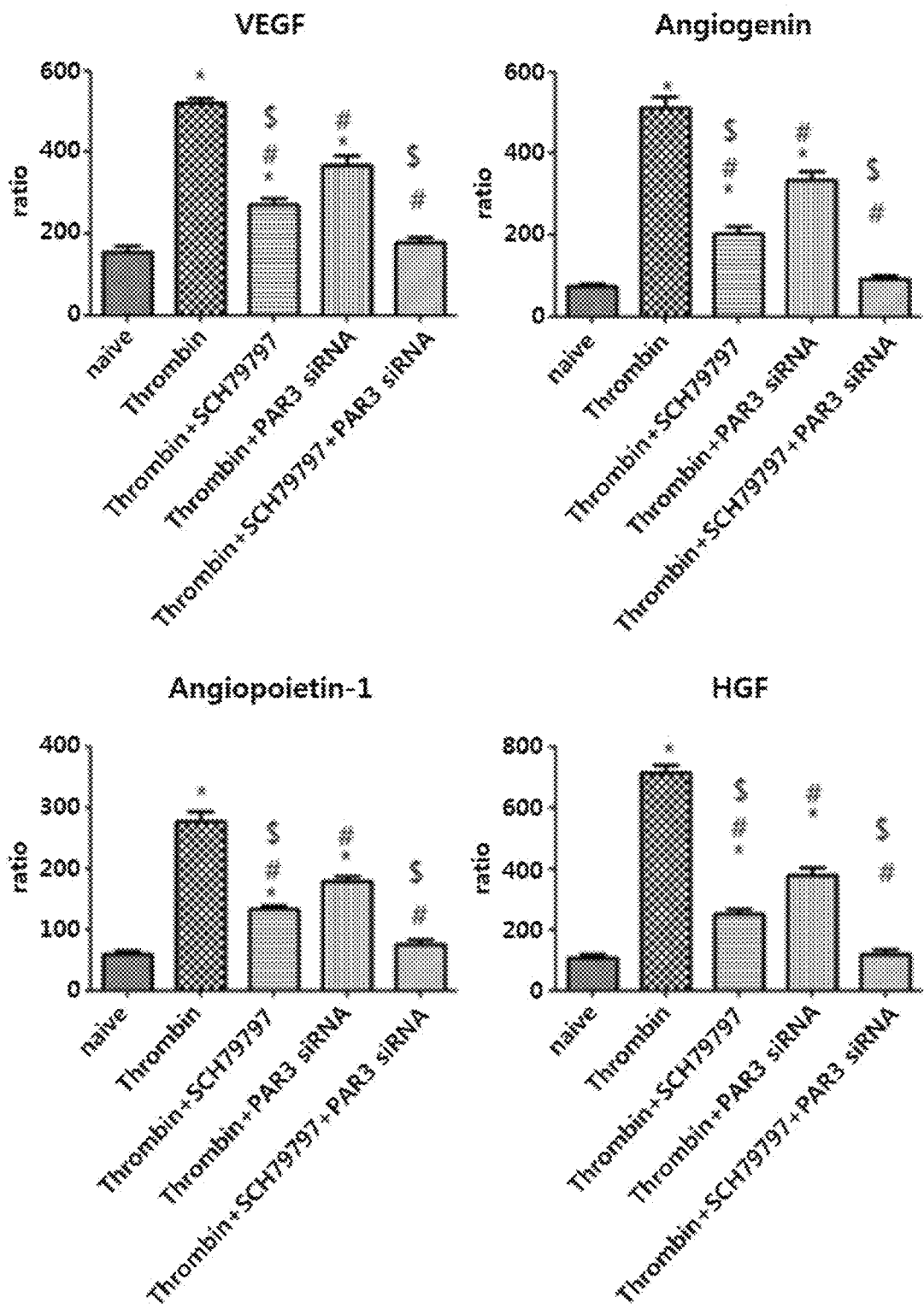
FIG. 5D illustrates ELISA measurement results showing the levels of proteins (VEGF, Angiogenin, Angiopoietin-1, and HGF) contained in extracellular vesicles in each of the same groups as those of FIG. 4A.

In addition, a change in the levels of proteins in EVs by PAR inhibitor treatment in the same groups as described above was analyzed. Specifically, as a result of measuring the levels of VEGF, angiogenin, angiopoietin-1, and HGF, it was confirmed as shown in FIG. 5D that the increase in the levels of proteins was significantly inhibited in the groups respectively treated with SCH79797 and PAR3 siRNA, was inhibited at a higher level in the case of SCH79797 treatment than in the case of transfection with PAR3 siRNA, and was inhibited at the highest level in the case of co-treatment with both materials. These results suggest that PAR-1-mediated signaling is strongly involved in EV production and increased levels of cargo proteins by thrombin pretreatment stimulation, and PAR3 signaling is partially involved therein.

The above description of the present disclosure is provided only for illustrative purposes, and it will be understood by one of ordinary skill in the art to which the present disclosure pertains that the invention may be easily modified into other specific forms without departing from the technical spirit or essential characteristics thereof. Thus, the embodiments described herein should be considered in an illustrative sense only and not for the purpose of limitation.

INDUSTRIAL APPLICABILITY

According to the present disclosure, by treating stem cells with thrombin and measuring the activation degrees of protease activated receptor (PAR)-mediated signaling pathways, stem cells having the ability to produce extracellular vesicles with high efficiency can be efficiently selected, and thus stem cells selected using this method can be effectively used for various applications in basic research and clinical fields. In addition, a novel material can be discovered by screening an inducer for promoting extracellular vesicle production using a method of measuring the activation levels of PAR-mediated signaling pathways after stem cells are treated with a specific material, and thus the discovered material can be effectively used for producing stem cells having the ability to produce extracellular vesicles with high efficiency, which can be used in basic research and clinical fields.

What is claimed is:

1. A method of selecting a stem cell having an ability to produce extracellular vesicles with high efficiency, the method comprising measuring an activation level of a protease-activated receptor (PAR)-mediated signaling pathway,
   wherein the PAR is PAR1 or PAR3,
   wherein the ability to produce extracellular vesicles with high efficiency is promotion of the production of extracellular vesicles or promotion of a level of a protein in extracellular vesicles, and
   wherein the measurement of the activation level of the PAR-mediated signaling pathway comprises the following processes:
   (a) culturing stem cells and then treating the stem cells with thrombin;
   (b) measuring an expression level of one or more selected from the group consisting of Ras-related protein Rab-5 (Rab-5), early endosome antigen-1 (EEA-1), phospho-extracellular signal-regulated kinase 1/2 (p-ERK1/2), and phospho-protein kinase B (p-AKT) in the thrombin-treated stem cells; and
   (c) selecting a stem cell in which the expression level has been increased, as a stem cell having an ability to produce extracellular vesicles with high efficiency.

2. The method of claim 1, wherein the protein comprises one or more selected from the group consisting of a vascular endothelial growth factor (VEGF), a hepatocyte growth factor (HGF), angiogenin, and angiopoietin-1.

3. The method of claim 1, wherein the stem cell is an embryonic stem cell or an adult stem cell.

4. The method of claim 3, wherein the adult stem cell comprises one or more selected from the group consisting of a mesenchymal stem cell, a human tissue-derived mesenchymal stromal cell, a human tissue-derived mesenchymal stem cell, and a multipotent stem cell.

5. The method of claim 4, wherein the mesenchymal stem cell is derived from one or more tissues selected from the group consisting of an umbilical cord, umbilical cord blood, bone marrow, fat, muscle, skin, an amniotic membrane, and a placenta.

6. The method of claim 1, wherein the thrombin is treated at 1 U/mL to 10 U/mL.

* * * * *